United States Patent [19]
Tsukada et al.

[11] Patent Number: 5,658,843
[45] Date of Patent: Aug. 19, 1997

[54] METHOD FOR PREPARING COPPER-CONTAINING HYDROGENATION REACTION CATALYST AND METHOD FOR PRODUCING ALCOHOL

[75] Inventors: Kiyoshi Tsukada; Yasuyuki Hattori; Taku Mimura; Osamu Tabata; Futoshi Nishigaki, all of Wakayama, Japan

[73] Assignee: Kao Corporation, Tokyo, Japan

[21] Appl. No.: 448,580

[22] PCT Filed: Jan. 20, 1994

[86] PCT No.: PCT/JP94/00077

§ 371 Date: Jun. 6, 1995

§ 102(e) Date: Jun. 6, 1995

[87] PCT Pub. No.: WO95/19844

PCT Pub. Date: Jul. 27, 1995

[51] Int. Cl.$^6$ .............................. B01J 23/72; B01J 23/70
[52] U.S. Cl. .............................. 502/345; 502/344; 502/53; 502/56; 568/864; 568/885
[58] Field of Search ..................... 502/345, 344, 502/53, 56; 568/864, 885

[56] References Cited

U.S. PATENT DOCUMENTS

| | | | |
|---|---|---|---|
| 4,537,876 | 8/1985 | Blum et al. | 502/342 |
| 4,918,248 | 4/1990 | Hattori et al. | 568/885 |
| 5,481,048 | 1/1996 | Tsukada et al. | 568/885 |

FOREIGN PATENT DOCUMENTS 2017682  10/1979  United Kingdom .

OTHER PUBLICATIONS

English Abstract of Japanese Document No. JP-A-5-177140 Jul. 1993.
English Abstract of Japanese Document No. JP-A-5-117185 May 1993.
English Abstract of Japanese Document No. JP-A-61-161146 Jul. 1986.
English Abstract of Japanese Document No. JP-A-62-298457 Dec. 1987.
English Abstract of Japanese Document No. JP-A-61-178037 Aug. 1986.
English Abstract of Japanese Document No. JP-A-1-127042 May 1989.
English Abstract of Japanese Document No. JP-A-2-26611 Jan. 1990.
English Abstract of Japanese Document No. JP-47-14113 no date.
English Abstract of German Document No. 3443277 Jun. 1985.
English Abstract of German Document No. 1768313 May 1977.

*Primary Examiner*—Glenn A. Caldarola
*Assistant Examiner*—Nadine Preisch
*Attorney, Agent, or Firm*—Birch, Stewart, Kolasch & Birch, LLP

[57] ABSTRACT

A method for preparing a copper-containing hydrogenation reaction catalyst includes the step of reducing a formed precursor of a copper-containing hydrogenation reaction catalyst with hydrogen gas or a mixture of hydrogen and inert gas by liquid phase reduction in a stream of a solvent. The reductive activation is carried out by the two steps of performing the first stage of liquid phase reduction by which the catalyst precursor is activated in the temperature range of from 20° to 140° C. so that at least 10% by weight of the copper oxide contained in the catalyst precursor can be reduced by the time when the temperature passes 140° C., and then performing the second stage of liquid phase reduction by which the catalyst precursor is further activated in the temperature range of from 140° to 250° C. The catalyst thus obtained has markedly improved catalytic activity and selectivity. An alcohol of high quality can be obtained at a high productivity using the catalyst in a fixed bed continuous reaction system.

13 Claims, 1 Drawing Sheet

METHOD FOR PREPARING COPPER-CONTAINING HYDROGENATION REACTION CATALYST AND METHOD FOR PRODUCING ALCOHOL

TECHNICAL FIELD

The present invention relates to a method for preparing a copper-containing hydrogenation reaction catalyst, and to a method for producing an alcohol. More specifically, it relates to a method for preparing a copper-containing hydrogenation reaction catalyst by a liquid phase reduction under specified temperature conditions, and to a method for producing an alcohol of high quality at a high productivity using the copper-containing hydrogenation reaction catalyst prepared by the above method, which has markedly improved catalytic activity and selectivity.

BACKGROUND ART

Since the 1930s a number of methods have been disclosed for producing aliphatic alcohols, alicyclic alcohols or aromatic alcohols by hydrogenating carboxylic acids or esters of carboxylic acids. In those methods, copper catalysts are mainly proposed for use in hydrogenation of esters of carboxylic acids, particularly fatty acid esters, and copper-chromium catalysts are commonly used for industrial purposes.

The conditions employed to activate these catalysts by reduction are determined depending on the form of catalysts and usage, reduction method and other factors. For example, when the fluidized bed reaction system is employed, a catalyst is used in a powder form. In Japanese Patent Laid-Open Nos. 1-305042, 5-177140 and 5-11718.5, it is stated that a catalyst may be activated by gas phase reduction or by liquid phase reduction in a solvent exemplified by hydrocarbons such as paraffin, ethers such as dioxane, alcohols and esters. Gas phase reduction, however, requires an additional apparatus other than the reactor for reductive activation of the powdery catalyst and further a surface stabilizing treatment for preventing the resulting copper from being oxidized by air. Because of these drawbacks of gas phase reduction, liquid phase reduction is generally employed in the fluidized bed reaction system. In this case, it is generally agreed that reduction is carried out preferably at a temperature of from 150° to 350° C. until hydrogen absorption has stopped. Since heat removal is easy in the case of powdery catalysts, local overheating can easily be prevented.

On the other hand, when a fixed bed reaction system is employed, gas phase reduction is exclusively used for the reductive activation of a formed catalyst, and for industrial purposes, it is common practice to carefully reduce a catalyst at a given temperature while supplying an inert gas containing several to several dozens percents of hydrogen, to prevent local overheating due to rapid reduction.

Reduction of copper oxide with hydrogen is generally known to generate a heat of reduction of 20 Kcal per mole of copper oxide and reduced copper thus obtained has a very low thermal stability. For this reason, it is important to gradually reduce the copper oxide while controlling heat generation to prevent the deterioration of its catalyst performance. When using a formed catalyst, in particular, this is critical because heat removal is difficult.

It is, therefore, very likely that when the catalyst is activated by gas phase reduction with a high concentration of hydrogen in a short time, a rapid heat generation considerably degrades catalyst performance, and that when a large amount of catalyst is activated by reduction in a short time on an industrial scale, a rapid rise in temperature causes a very dangerous situation. For this reason, it is common practice to use a low concentration of hydrogen over a long period of time for activation of catalysts containing copper oxide by gas phase reduction. For example, Japanese Patent Laid-Open No. 61-161146 states that it takes as long as 4 to 14 days for catalytic activation by such reduction, suggesting a disadvantage of gas phase reduction in view of alcohol productivity.

Also, DT 1768313 discloses a method for reductive activation of a copper-zinc oxide catalyst, in which the catalyst is gradually reduced at a temperature of between 120° and 240° C. in a hydrogen-containing nitrogen gas stream and finally treated with high-pressure hydrogen at a temperature of between 250° and 300° C. for 1 to 2 hours. Japanese Patent Laid-Open No. 62-298457 states that a copper-chromium oxide catalyst can be activated by raising a temperature from 130° C. to 200° C. at a rate of 10° C./hr and keeping it at 200° C. for 12 hours in a nitrogen gas stream containing 1% by volume hydrogen. Also, DE 3443277A1 discloses a method for reductive activation of a copper-zinc oxide catalyst, in which the catalyst is reduced at 200° C. in a nitrogen gas stream containing 5% by volume hydrogen for 16 hours and then further reduced with pure hydrogen at 200° C. for 16 hours. Japanese Patent Laid-Open No. 61,178037 states that a copper oxide-magnesium silicate catalyst can be activated by reducing the catalyst at 200° C. in a nitrogen gas stream containing 1 to 2% by volume hydrogen For 60 hours. In addition, Japanese Patent Laid-Open No. 1-127042, which discloses a method for reductive activation of copper-chromium oxide and reviews the prior arts, indicates that all methods require catalyst reduction temperatures of not lower than 150° C.

Although gas phase reduction is commonly used in the fixed bed reaction system, several methods are also known to activate a catalyst precursor containing copper oxide by liquid phase reduction. For example, Japanese Patent Laid-Open Nos. 5-177140 and 5-117185 propose to activate a copper-zinc oxide catalyst at 200° C. in an autoclave by the batch reaction method in liquid phase. Also, British Patent Publication No. 385625 describes a method of liquid phase reduction of a copper-chromium catalyst at 325° C. in an ester flow of a liquid hourly space velocity of 8.0 by the fixed bed reaction system, followed by hydrogenating an ester. Also, Japanese Patent Laid-Open No. 47-14113 discloses a method of liquid phase reduction of a copper-chromium catalyst at 200° C. in a lactone flow of a liquid hourly space velocity of 0.67 by the fixed bed reaction system, followed by hydrogenating a lactone. According to Japanese Patent Laid-Open No. 2-26611, the reduction of a catalyst containing copper oxide can be carried out after an ester, the starting material, has been supplied.

However, all these methods for catalytic activation by liquid phase reduction have proved to lack any advantages or superiority over those by gas phase reduction, as Japanese Patent Laid-Open No. 2-26611 describes that "reduction of the catalyst's copper component by these methods is not complete and somewhat difficult to control."

DISCLOSURE OF INVENTION

Accordingly, it is an object of the present invention to provide a method for preparing a copper-containing hydrogenation reaction catalyst with markedly improved catalytic activity and selectivity by liquid phase reduction.

It is another object of the present invention to provide a method for producing an alcohol of high quality at a high productivity using the copper-containing hydrogenation reaction catalyst prepared by the above method.

In hydrogenating an organic carboxylic acid or ester of organic carboxylic acid, preferably fats and oils or fatty acid ester, by the fixed bed continuous reaction system to produce the corresponding alcohol, the present inventors brought hydrogen gas or a mixture of hydrogen and inert gas into contact with a catalyst precursor containing copper oxide in a solvent which does not react with copper oxide or metallic, copper, to perform the first stage of liquid phase reduction at a temperature of from 20° to 140° C., and subsequently raised the temperature to a range of from 140° C. to 250° C. to perform the second stage of liquid phase reduction. The inventors have found that the method makes it possible to very rapidly and easily obtain a catalyst with high activity and selectivity for alcohol production which cannot be obtained by any one of the conventional methods for reductive activation by gas phase reduction or liquid phase reduction. The inventors have made further investigations based on this finding, and have completed the present invention.

Specifically, the present invention relates to:

(1) a method for preparing a copper-containing hydrogenation reaction catalyst by reducing a precursor of a formed copper-containing hydrogenation reaction catalyst with hydrogen gas or a mixture of hydrogen and inert gas by liquid phase reduction in a stream of a solvent which does not react with copper oxide or metallic copper, which comprises the steps of performing the first stage of liquid phase reduction by which the catalyst precursor is activated in the temperature range of from 20° to 140° C. so that at least 10% by weight of the copper oxide contained in the catalyst precursor can be reduced by the time when the temperature passes 140° C.; and then performing the second stage of liquid phase reduction by which the catalyst precursor is further activated in the temperature range of from 140° to 250° C.; and (2) a method for producing an alcohol, comprising the step of reducing an organic carboxylic acid or ester of organic carboxylic acid by catalytic reduction with hydrogen in a fixed bed continuous reaction system, wherein the catalyst prepared by the method of (1) above is used.

According to the method for preparing a copper-containing hydrogenation reaction catalyst of the present invention, in comparison with conventional methods for catalyst activation based on gas phase reduction or liquid phase reduction, not only the catalyst activation process time can be significantly reduced, but also catalytic activity and selectivity can be remarkably improved. The method of alcohol production in the present invention, using the above catalyst, makes it possible to produce an alcohol of high quality at a very high efficiency on an industrial scale.

BEST MODE FOR CARRYING OUT THE INVENTION

Figure 1:
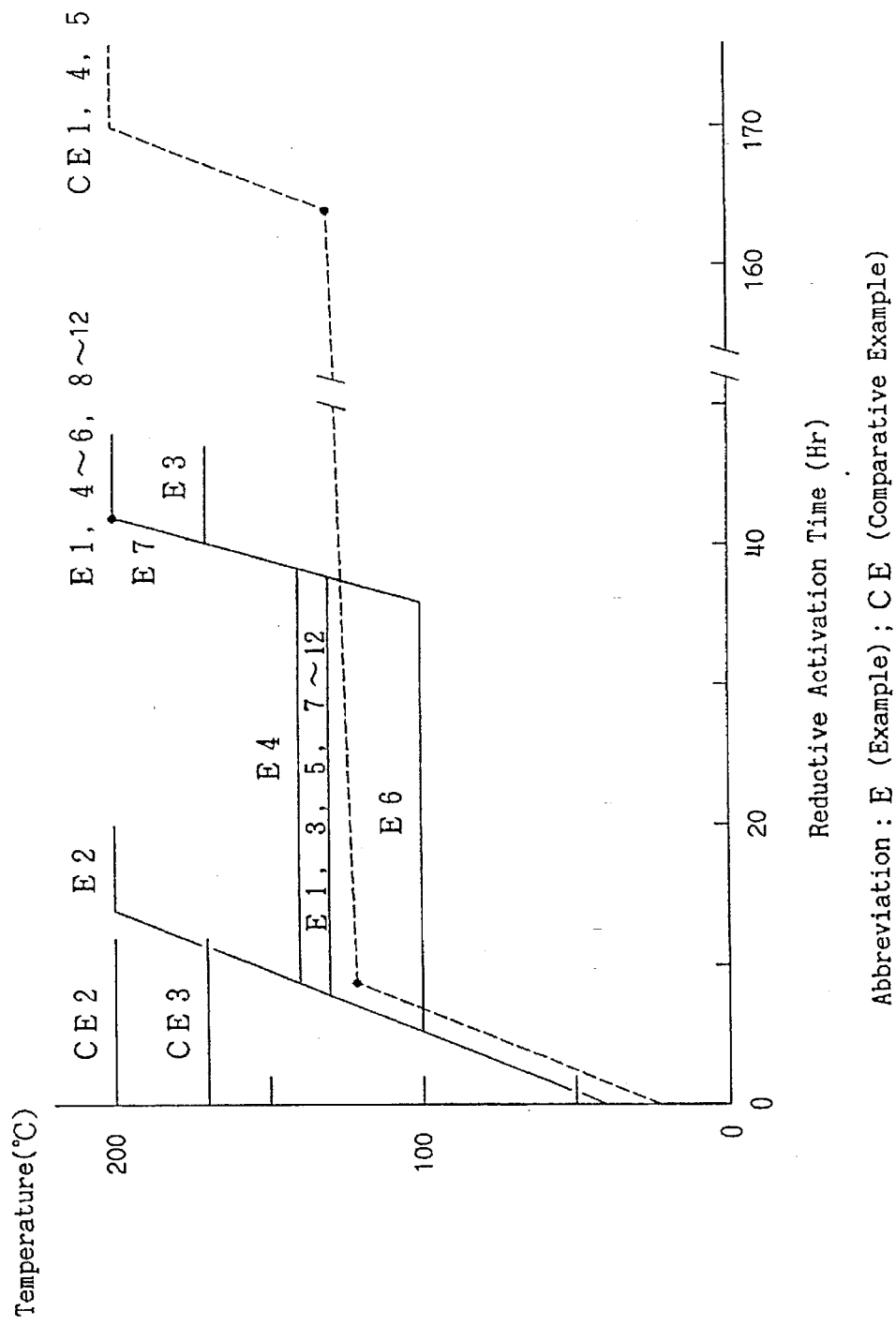
FIG. 1 is a graphic illustration of the reduction temperature and time employed in each of the Examples and Comparative Examples

The present invention is described in detail below. The method of the present invention for preparing a copper-containing hydrogenation reaction catalyst is carried out by reducing a formed precursor of a copper-containing hydrogenation reaction catalyst with hydrogen gas in a stream of a solvent which does not react with copper oxide or metallic copper (hereinafter referred to as the inert solvent).

Precursors of copper-containing hydrogenation reaction catalysts include, but not limited to, those for such as copper-chromium oxide catalysts, copper-zinc oxide catalysts, copper-iron oxide catalysts, copper-aluminum oxide catalysts and copper-silica oxide catalysts. It is preferable, however, that the content of copper oxide falls within the range of from 5 to 98% by weight, more preferably from 20 to 98% by weight, particularly preferably from 20 to 80% by weight per the total weight of the catalyst precursor. These metal catalyst precursors may be carried on carriers such as silica, alumina, zirconium oxide, titanium oxide and silica-alumina. In such cases, the total weight of the catalyst precursor as mentioned herein includes the weight of the carrier.

It can be optionally chosen which shape the catalyst precursor will take, as long as operation of the fixed bed reactor is not interfered with. Usually, cylindrically tableted or extruded catalyst precursors, or 1 to 20 mm spherically formed catalyst precursors are preferably used, since their production is easy and inexpensive.

Also, the inert solvent mentioned herein is a solvent which does not dissolve or irreversibly adsorb copper oxide or metallic copper and which does not form a compound with copper. Such solvents remains to be in a liquid state under the reducing conditions for activating the catalyst precursor, and preferably include glyceride oils, esters, alcohols, hydrocarbons or the like. Most preferable solvents include glyceride oils, fatty acid esters, aliphatic alcohols and hydrocarbons which do not adversely affect the quality of the desired alcohol produced according to the present invention, and these solvents may be used singly or in combination. Specifically, the glyceride oils are exemplified by monoglycerides, diglycerides and triglycerides comprising fatty acids having 6 to 22 carbon atoms. Such fatty acids include natural fatty acids of plant or animal origin derived from coconut oil, palm kernel oil, palm oil, beef tallow, lard and the like, and synthetic fatty acids. The fatty acid esters are exemplified by those formed between a fatty acid having at least one fatty acid group and 2 to 22 carbon atoms and an aliphatic alcohol having 1 to 22 carbon atoms. For example, esters formed between one of the above mentioned fatty acids and an aliphatic alcohol such as methanol, ethanol, propanol, butanol, hexanol, octanol, decanol, lauryl alcohol, myristyl alcohol, cetyl alcohol, stearyl alcohol and isostearyl alcohol. The aliphatic alcohols used as solvents are exemplified by those having 2 to 22 carbon atoms and at least one hydroxyl group which is in a liquid state under the reducing conditions for activating the catalyst precursor. Such aliphatic alcohols include octanol, decanol, lauryl alcohol, myristyl alcohol, cetyl alcohol, stearyl alcohol and isostearyl alcohol. The hydrocarbons are exemplified by liquid paraffin and cyclic hydrocarbons such as cyclohexane, cyclooctane, decalin, benzene, toluene, xylene and naphthalene.

However, other inert solvents may also be used, as long as the residual impurities from the solvent do not significantly affect the quality of the alcohol produced. Such solvents include ethers, aldehydes and ketones which are in a liquid state under the reducing conditions for activating the catalyst precursor. In addition, the alkyl group moiety of these organic compounds, including the above-mentioned esters and alcohols, comprises one or more kinds selected from the group consisting of straight chain, branched chain, alicyclic ring, and aromatic ring.

The rate for supplying such a solvent is preferably 0.1 to 5.0/hr, more preferably 0.1 to 3.0/hr as a liquid hourly space velocity. When the supply rate is lower than 0.1/hr, the catalyst precursor is unevenly wetted by the solvent so that the catalyst precursor may partially undergo gas phase reduction. When the supply rate exceeds 5.0/hr, the required amount of solvent becomes large and thus it is economically undesirable, though catalyst reduction is not hampered at all.

The method of the present invention for preparing a copper-containing hydrogenation reaction catalyst is carried out while supplying hydrogen gas or a mixture of hydrogen and inert gas, as a reducing agent to contact a catalyst precursor therewith.

The inert gas for diluting hydrogen may include nitrogen, helium, argon, methane and the like.

The hydrogen concentration in the gas mixture is optionally chosen within the range of from not less than 0.1% by volume to less than 100% by volume, but it is desirable from the viewpoint of the time required for the activation to set the hydrogen concentration at such level that the partial hydrogen pressure will be one atom or higher.

Preferably, the gas is supplied under normal pressure or increased pressure up to 300 atm in a stream of the solvent. Gas supply pressures above 300 atm are economically disadvantageous because of increased equipment burden, though the effect of the invention can be obtained.

Also, the gas is preferably supplied at a gas hourly space velocity of from 50 to 10000/hr, more preferably from 100 to 5000/hr. When gas hourly space velocities are below 50/hr, it is difficult to adequately remove the heat and the water produced upon reduction, resulting in decreased catalyst performance. Gas hourly space velocities exceeding 10000/hr are disadvantageous in view of equipment requirements.

In the present invention, the temperature at which reduction is carried out is very important. This invention is characterized in that a catalyst precursor is partially reduced by liquid phase reduction within the temperature range of from 20° to 140° C. (hereinafter referred to as the first stage of liquid phase reduction or the first stage reduction) and then subjected to the reduction to completion within the raised temperature range of from 140° to 250° C. (hereinafter referred to as the second stage of liquid phase reduction or the second stage reduction), while supplying a solvent and a gas as stated above. When a liquid phase reduction is directly carried out at a temperature of not lower than 140° C. by the conventional method without the first stage of liquid phase reduction in the temperature range of from 20° to 140° C., the activated metallic copper is considerably damaged by the heat generated with rapid reduction of the catalyst precursor, resulting in significant deterioration of the catalyst performance.

For example, as stated above, in the hydrogenation reaction of butyl acetate disclosed in British Patent Publication No. 385625, a copper-chromium catalyst is subjected to liquid phase reduction at 325° C., and in the hydrogenation reaction of lactone disclosed in Japanese Patent Laid-Open No. 47-14113, a copper-chromium catalyst is subjected to liquid phase reduction at 200° C. Both fail to show an advantage in catalyst performance. On the other hand, in the present invention remarkably improved catalytic activity and selectivity of the catalyst can be achieved by conducting liquid phase reduction of a catalyst precursor in two different temperature ranges, as described in Examples given below.

Here, the liquid phase reduction in the present invention may be carried out by keeping a constant temperature for most of the reduction time, or raising the temperature over the period of the reduction time. Alternatively, it may be carried out in combination, i.e., by keeping a constant temperature and raising the temperature. The temperature may be raised continuously or discontinuously, and the heating speed may not necessarily be constant. The effect of the present invention is not influenced by whether the temperature is kept constant for a certain period of time or it is kept changing.

Next, the first stage of liquid phase reduction is described in more detail below. In the first stage of liquid phase reduction, it is important to carry out the reduction over a given period of time within the temperature range of from 70° to 140° C., the range where practically efficient liquid phase reduction can be carried out. Specifically, the first stage of liquid phase reduction may be performed by raising the temperature continuously or discontinuously within this temperature range (70° to 140° C.) over a time period of normally not less than 1.5 hours, preferably 3 to 50 hours.

In the present specification, the temperature most involved in the first stage of liquid phase reduction is referred to as the first stage reduction temperature $T_1$. For example, when the temperature is raised from 40° C. at a rate of 10° C./hr and kept at 130° C. for 30 hours and subsequently raised to 140° C. at a rate of 10° C./hr in the first stage of liquid phase reduction, the first stage of reduction temperature $T_1$ is 130° C., since the first stage of liquid phase reduction is carried out mainly at 130° C. When the temperature is raised at a constant rate within the temperature range of from 70° to 140° C., the first stage reduction temperature $T_1$ is to be from 70° to 140° C. Thus, $T_1$ is not necessarily a constant temperature. However, such a case is also included within the scope of the present invention.

When reduction is carried out over a given period of time within the temperature range of from 70° to 140° C. as stated above, the temperature may be gradually raised over the given period of time, or it may be maintained at a given level within the temperature range of from 70° to 140° C. for at least 0.5 hours as stated above. Also, in the first stage of liquid phase reduction, it is desirable to start heating at a temperature of from 20° to 50° C., because it is important to start reduction of a catalyst precursor under as mild conditions as possible for enhancing catalyst performance.

Here, the rate at which the temperature is raised (hereinafter referred to as heating rate) is normally 0.5° to 40° C./hr, preferably 1° to 30° C./hr, and most preferably 5° to 20° C./hr. Heating rates below 0.5° C./hr are disadvantageous in that too much time is required for the reductive activation of the catalyst precursor, though the effect of the present invention can be obtained. Heating rates exceeding 40° C./hr are also disadvantageous in that accumulation of heat of reduction generated with rapid catalyst reduction causes a rapid rise in temperature and makes it difficult to control the reducing reaction.

In the first stage of liquid phase reduction, not less than 10% by weight, preferably 20 to 95% by weight of the copper oxide contained in the catalyst precursor is reduced by the time when the temperature passes 140° C.

In the second stage of liquid phase reduction, which follows the completion of the first stage of liquid phase reduction, further liquid phase reduction is carried out to complete the reduction by hydrogen treatment while raising the temperature within the temperature range of from 140° to 250° C. The temperature is raised continuously or discontinuously, and the heating rate, not subject to limitation, is preferably 0.5° to 40° C./hr. Also, it may be kept at a given temperature for a given period of time.

In the present specification, the temperature most involved in the second stage of liquid phase reduction is referred to as the second stage reduction temperature $T_2$, which corresponds to $T_1$ in the first stage of liquid phase reduction. For example, when the second stage of liquid phase reduction, after completion of the first stage of liquid phase reduction, is subsequently carried out by raising the temperature to 200° C. at a rate of 10° C./hr and keeping the temperature at 200° C. for 6 hours, the second stage of reduction temperature $T_2$ is 200° C., since the second stage of liquid phase reduction is carried out mainly at 200° C.

The second stage of liquid phase reduction is to promote the reduction and achieve an early completion of the reduction, which can provide a catalyst with high catalytic activity.

The copper-containing hydrogenation reaction catalyst thus obtained by the method of the present invention can be used mainly for alcohol production in the fixed bed continuous reaction system, and it can also be used for various hydrogenation reactions such as aldehyde group or ketone group hydrogenation, olefin hydrogenation and nitro group hydrogenation. Therefore, when liquid phase reduction of a precursor of a copper-containing hydrogenation reaction catalyst is carried out in a fixed bed reactor for continuous reaction, the resulting activated catalyst can be directly used for the subsequent production of alcohols or other products.

The method for producing an alcohol of the present invention is characterized in that a copper-containing hydrogenation reaction catalyst activated by the above-described method is used to produce an alcohol by catalytic reduction of an organic carboxylic acid or ester of organic carboxylic acid with hydrogen in a fixed bed continuous reaction system.

Organic carboxylic acids used as the starting material include natural fatty acids of animal or plant origin derived from coconut oil, palm kernel oil, palm oil, beef tallow, lard and the like, and synthetic fatty acids. The preferred ester of organic carboxylic acid is fats and oils or fatty acid ester. The fats and oils are exemplified by monoglycerides, diglycerides and triglycerides comprising saturated or unsaturated fatty acids having 6 to 22 carbon atoms. The fatty acid ester is exemplified by straight or branched, or unsaturated fatty acid esters having one or more carbon atoms and one or more ester groups. Such fatty acid esters include formates, acetates, caproates, caprylates, caprates, undecenates, laurates, myristates, palmitates, stearates, isostearates, oleates, arachates, behenates, oxalates, maleates, adipates and sebacates. Here, the alcohol moiety of the fatty acid ester, not subject to limitation, comprises an aliphatic alcohol having 1 to 22 carbon atoms. Also, the ester to be hydrogenated in the present invention is not limited to fatty acid esters, and may be any one of alicyclic carboxylic acid esters such as cyclohexanecarboxylate, and aromatic carboxylic acid esters such as benzoate and phthalate, and derivatives thereof.

In the present invention, the fixed bed continuous reaction system is employed to hydrogenate the above-described organic carboxylic acid or ester of organic carboxylic acid. Here, it is preferred to prepare a catalyst in a fixed bed continuous reactor by the foregoing method of the present invention, and subsequently hydrogenate these materials in the same reactor to produce an alcohol. This is industrially advantageous. Although a solvent may be used for the hydrogenation reaction, it is desirable to carry out the reaction in the absence of a solvent in view of productivity. When a solvent is used, it is chosen from the group of solvents which do not adversely affect the reaction, such as alcohols, dioxane and paraffin. Reaction temperature is normally 130° to 300° C., preferably 160° to 250° C., reaction pressure being 0.1 to 300 kg/cm². Also, the liquid hourly space velocity for the starting material supply is determined optionally according to reaction conditions, and is preferably within the range of from 0.2 to 5.0/hr in view of productivity or reactivity.

The present invention is hereinafter described in more details by means of the following working examples and comparative examples, but the present invention is not limited by them.

EXAMPLE 1

First, a catalyst precursor comprising CuO, ZnO and BaO carried on $TiO_2$ was prepared by the method described in Example 5 of Japanese Patent Laid-Open No. 5-177140.

The obtained precursor powder was cylindrically tableted and then calcined at 400° C. for 2 hours to yield a formed catalyst precursor having a diameter of 3 mm, a height of 3 mm and the following weight composition:

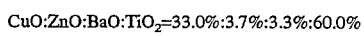

$CuO:ZnO:BaO:TiO_2=33.0\%:3.7\%:3.3\%:60.0\%$

After 30 cc of the thus-obtained formed catalyst precursor was packed in a fixed bed high-pressure flow reactor, hydrogen gas (100% concentration) was introduced at a flow rate of 37 NL/hr (a gas hourly space velocity of 1230/hr) at a temperature of 40° C., and then lauryl alcohol was supplied at a flow rate of 15 cc/hr (a liquid hourly space velocity of 0.5/hr). After the liquid and gas flow rates were stabilized, the temperature was raised at a rate of 10° C./hr under a hydrogen pressure of 20 kg/cm² (gauge pressure) and maintained at 130° C. for 30 hours to carry out the first stage of liquid phase reduction. Subsequently, the temperature was further raised at a rate of 10° C./hr, and when it reached 200° C., the catalyst precursor was kept at this temperature level for 6 hours for the second stage of liquid phase reduction.

After completion of the reductive activation of the catalyst precursor, the lauryl alcohol was replaced with a fatty acid methyl ester having a chain length distribution of from 8 to 18 carbon atoms, and a hydrogenation reaction was carried out at 230° C. while supplying hydrogen in an amount of 25 mole per mole of the fatty acid methyl ester under a pressure of 200 kg/cm² and at a liquid hourly space velocity of 1.0/hr.

The catalytic activity was determined as a constant for the primary reaction rate per unit volume of the formed catalyst. Also, the reaction selectivity is expressed in terms of the amount of byproducts such as hydrocarbons and ether compounds determined by gas chromatography. The results are shown in Table 1.

TABLE 1

| | Conditions for reductive activation of catalyst | | | | | | Reduction | Catalyst performance | |
|---|---|---|---|---|---|---|---|---|---|
| | Atmosphere | LHSV | Pressure (kg/cm$^2$) | H$_2$ concentration (%) | T$_1$ (°C.) | T$_2$ (°C.) | percent (%) | Relative activity | Selectivity |
| Example 1 | Liquid phase | 0.5 | 20 | 100 | 130 | 200 | 90 | 1.23 | 0.43 |
| Comparative Example 1 | Gas phase | — | 15 | 1.3–5.0 | 120–130 | 200 | 100 | 1 | 1 |
| Example 2 | Liquid phase | 0.5 | 3 | 100 | 90–140 | 200 | 15 | 1.22 | 0.54 |
| Comparative Example 2 | Liquid phase | 0.5 | 20 | 100 | — | 200 | 0 | 0.75 | 1.2 |
| Comparative Example 3 | Liquid phase | 0.5 | 20 | 100 | — | 170 | 0 | 0.87 | 1.1 |
| Example 3 | Liquid phase | 2.0 | 200 | 100 | 130 | 170 | 95 | 1.20 | 0.53 |
| Example 4 | Liquid phase | 0.5 | 20 | 15 | 140 | 200 | 95 | 1.43 | 0.44 |
| Example 5 | Liquid phase | 0.2 | 20 | 50 | 130 | 200 | 55 | 1.38 | 0.44 |
| Example 6 | Liquid phase | 0.5 | 20 | 50 | 100 | 200 | 75 | 1.50 | 0.44 |
| Example 7 | Liquid phase | 0.5 | 20 | 100 | 130 | 200 | 90 | 1.20 | 0.45 |

Remarks:
Solvent for liquid phase: lauryl alcohol
LHSV: Liquid hourly space velocity
Reduction percent: percent of copper oxide reduced at the time when the temperature passes 140° C., which is calculated from the amount of water produced by reduction (% by weight)
Relative activity: activity relative to that of the catalyst reduced by gas phase reduction (Comparative Example 1). The higher value means the better activity.
Selectivity: relivite selectivity calculated on the basis of the amount of byproducts produced using the catalyst reduced by gas phase reduction (Comparative Example 1). The smaller value means the better selectivity.

Comparative Example 1

The formed catalyst precursor described in Example 1 was packed in a reactor in the same manner as in Example 1. Then, a stream of 1.3 to 5.0% by volume of nitrogen-diluted hydrogen was introduced at a gas hourly space velocity of 250 hr under a pressure of 15 kg/cm$^2$ (gauge pressure) while raising the temperature from a room temperature to 120° 130° C. at a rate of 10° C./hr. While maintaining the temperature at the reached level, the catalyst precursor was subjected to a conventional gas phase reduction for 157 hours. Thereafter, the temperature was raised to 200° C. at a rate of 10° C./hr, and reduction was further carried out for 6 hours while keeping the temperature at 200° C. Using the activated catalyst thus obtained, hydrogenation of a fatty acid methyl ester was carried out according to the method described in Example 1. The results are shown in Table 1.

EXAMPLE 2

The formed catalyst precursor described in Example 1 was packed in a reactor in the same manner as in Example 1. In a stream of hydrogen flowing at a rate of 37 NL/hr at 40° C. under a pressure of 3 kg/cm$^2$ (gauge pressure), lauryl alcohol was introduced, and the temperature was raised at a rate of 10° C./hr. After reaching 140° C., the temperature was continued to be raised until it became 200° C. While keeping the temperature at 200° C. for 6 hours, the catalyst precursor was subjected to the second stage of liquid phase reduction. Using the activated catalyst thus obtained, hydrogenation of a fatty acid methyl ester was carried out according to the method described in Example 1. The results are shown in Table 1.

Comparative Example 2

In reductive activation of a catalyst precursor as described in Example 1, lauryl alcohol was introduced while flowing a nitrogen gas at a rate of 37 NL/hr. The temperature was raised at a rate of 10° C./hr. Immediately after the temperature reached 200° C., hydrogen gas was introduced at a flow rate of 37 NL/hr under a pressure of 20 kg/cm$^2$ (gauge pressure) in place of nitrogen gas, and reductive activation of a catalyst precursor was conducted at 200° C. for 12 hours. Using the activated catalyst thus obtained, hydrogenation of a fatty acid methyl ester was carried out according to the method described in Example 1. The results are shown in Table 1.

Comparative Example 3

In reductive activation of a catalyst precursor as described in Example 1, lauryl alcohol was introduced while flowing a nitrogen gas at a rate of 37 NL/hr. The temperature was raised to 170° C. at a rate of 10° C./hr. Then, reductive activation of a catalyst precursor was carried out with hydrogen gas in the same way as in Comparative Example 2. Using the activated catalyst thus obtained, hydrogenation of a fatty acid methyl ester was carried out according to the method described in Example 1. The results are shown in Table 1.

EXAMPLE 3

The first stage of liquid phase reduction of a catalyst precursor was conducted under the same conditions as those in Example 1 except that lauryl alcohol was introduced at a flow rate of 60 cc/hr (a liquid hourly space velocity of 2.0/hr) and that the hydrogen pressure was set at 200 kg/cm$^2$ (gauge pressure). After the completion of the first stage reduction, the temperature was raised to 170° C. at a rate of 10° C./hr, and the catalyst precursor was subjected to the second stage reduction at 170° C. for 6 hours. Using the activated catalyst thus obtained, hydrogenation of a fatty acid methyl ester was carried out according to the method described in Example 1. The results are shown in Table 1.

EXAMPLE 4

The reductive activation of a catalyst precursor was conducted under the same conditions as those in Example 1 except that the hydrogen gas used in the first and second stage reduction in Example 1 was replaced with a gas mixture of hydrogen and nitrogen having a hydrogen concentration of 15% by volume (a hydrogen partial pressure of 3 kg/cm$^2$) and that the first stage reduction temperature $T_1$ was 140° C. Using the activated catalyst thus obtained, hydrogenation of a fatty acid methyl ester was carried out according to the method described in Example 1. The results are shown in Table 1.

EXAMPLE 5

The reductive activation of a catalyst precursor was conducted under the same conditions as those in Example 1 except that the flow rate of lauryl alcohol was 6 cc/hr (a liquid hourly space velocity of 0.2/hr) and that the hydrogen gas used in the first and second stage reduction in Example 1 was replaced with a gas mixture of hydrogen and nitrogen having a hydrogen concentration of 50% by volume (a hydrogen partial pressure of 10 kg/cm$^2$). Using the activated catalyst thus obtained, hydrogenation of a fatty acid methyl ester was carried out according to the method described in Example 1. The results are shown in Table 1.

EXAMPLE 6

The reductive activation of a catalyst precursor was conducted under the same conditions as those in Example 1 except that the hydrogen concentration of hydrogen gas used in the first and second stage reduction was 50% by volume and that $T_1$ was 100° C. Using the activated catalyst thus obtained, hydrogenation of a fatty acid methyl ester was carried out according to the method described in Example 1. The results are shown in Table 1.

EXAMPLE 7

In the reductive activation of a catalyst precursor as described in Example 1, the first stage reduction of a catalyst precursor was carried out at 130° C. for 30 hours, and then the temperature was raised at a rate of 10° C./hr, while continuing reduction. The reduction was terminated when the temperature reached 200° C. Using the activated catalyst thus obtained, hydrogenation of a fatty acid methyl ester was carried out according to the method described in Example 1. The results are shown in Table 1.

EXAMPLE 8

The reductive activation of a catalyst precursor was conducted under the same conditions as those in Example 1 except that coconut oil refined by de-acidification (a saponification value of 224, an acid value of 0.02, a hydroxyl value of 4.9) was used in place of lauryl alcohol. Using the activated catalyst thus obtained, hydrogenation of a fatty acid methyl ester was carried out according to the method described in Example 1. The results are shown in Table 2.

TABLE 2

| | Conditions for reductive activation of catalyst | | | | | | Reduction | Catalyst performance | |
|---|---|---|---|---|---|---|---|---|---|
| | Atmosphere | LHSV | Pressure (kg/cm$^2$) | H$_2$ concentration (%) | $T_1$ (°C.) | $T_2$ (°C.) | percent (%) | Relative activity | Selectivity |
| Example 8 | Coconut oil | 0.5 | 20 | 100 | 130 | 200 | 85 | 1.22 | 0.51 |
| Example 9 | Ester | 0.5 | 20 | 100 | 130 | 200 | 85 | 1.24 | 0.50 |
| Example 10 | Paraffin | 0.5 | 20 | 100 | 130 | 200 | 90 | 1.27 | 0.52 |

Relative activity, selectivity: Relative values based upon the catalyst performance obtained in Comparative Example 1.

EXAMPLE 9

The reductive activation of a catalyst precursor was conducted under the same conditions as those in Example 1 except that the fatty acid methyl ester subjected to the hydrogenation reaction was used in place of lauryl alcohol. Using the activated catalyst thus obtained, hydrogenation of a fatty acid methyl ester was carried out according to the method described in Example 1. The results are shown in Table 2.

EXAMPLE 10

The reductive activation of a catalyst precursor was conducted under the same conditions as those in Example 1 except that liquid paraffin was used in place of lauryl alcohol. After the activated catalyst thus obtained was washed with the fatty acid methyl ester to be hydrogenated in the subsequent hydrogenation reaction in order to remove liquid paraffin adhered thereto, hydrogenation of a fatty acid methyl ester was carried out using the activated catalyst thus obtained according to the method described in Example 1. The results are shown in Table 2.

EXAMPLE 11

A commercially available copper-chromium catalyst precursor (Cu:Cr=1:1, atomic ratio), which was a cylindrical tablet having a diameter of 3 mm and a height of 3 mm, was packed in a fixed bed high pressure flow reactor in the same manner as described in Example 1. Reductive treatment of the catalyst precursor was carried out under the same conditions as in Example 1. Using the activated catalyst thus obtained, hydrogenation of a fatty acid methyl ester was carried out according to the method described in Example 1. The results are shown in Table 3.

TABLE 3

| | Conditions for reductive activation of catalyst | | | | | | Reduction | Catalyst performance | |
|---|---|---|---|---|---|---|---|---|---|
| | Atmosphere | LHSV | Pressure (kg/cm$^2$) | H$_2$ concentration (%) | T$_1$ (°C.) | T$_2$ (°C.) | percent (%) | Relative activity | Selectivity |
| Example 11 | Liquid phase | 0.5 | 20 | 100 | 130 | 200 | 95 | 1.25 | 0.55 |
| Comparative Example 4 | Gas phase | — | 15 | 1.3–5.0 | 130 | 200 | 100 | 1 | 1 |

Relative activity, selectivity: Relative values based upon the catalyst performance of the catalyst activated by gas phase reduction in Comparative Example 4. Catalyst: Copper-chromium catalyst Comparative Example 4

The formed catalyst precursor described in Example 11 was subjected to gas phase reduction under the same conditions as in Comparative Example 1. Using the catalyst thus activated by gas phase reduction, hydrogenation of a fatty acid methyl ester was carried out according to the method described in Example 1. The results are shown in Table 3.

EXAMPLE 12

The powder of a catalyst precursor prepared by the method disclosed in Example 1 of Japanese Patent Examined Publication No. 5850775 was molded by extrusion using bentonite to yield a needle shaped catalyst precursor having a length of 5 mm, a diameter of 2 mm and the following weight composition:

Cu:Fe:Al=1:1.1:1.2 (atomic ratio).

After 30 cc of the thus obtained formed catalyst precursor was packed in a fixed bed high-pressure flow reactor in the same manner as described in Example 1, reduction treatment was carried out under the same conditions as in Example 1. Using the activated catalyst thus obtained, hydrogenation of a fatty acid methyl ester was carried out according to the method described in Example 1. The results are shown in Table 4.

reaction catalyst of the present invention are excellent in relative activity and selectivity. On the other hand, the catalysts obtained by gas phase reduction (Comparative Examples 1, 4, 5) and all the catalysts obtained by liquid phase reduction carried out only within the T$_2$ temperature range (Comparative Examples 2, 3) proved to be inferior in relative activity and selectivity.

INDUSTRIAL APPLICABILITY

The catalyst prepared by the method of the present invention has markedly improved catalytic activity and selectivity. This catalyst is useful to produce an alcohol of high quality at a high productivity.

We claim:

1. A method for preparing a copper-containing hydrogenation reaction catalyst by reducing a formed precursor of a copper-containing hydrogenation reaction catalyst with hydrogen gas or a mixture or hydrogen and inert gas by liquid phase reduction in a stream of a solvent which does not react with copper oxide or metallic copper, which comprises the steps of performing the first stage of liquid phase reduction by which the catalyst precursor is activated in the temperature range of from 20° to 140° C. so that at least 10% by weight of the copper oxide contained in the catalyst precursor can be reduced by the time when the temperature passes 140° C.; and then performing the second stage of liquid phase reduction by which the catalyst precursor is further activated in the temperature range of from 140° to 250° C.

2. The method according to claim 1, wherein the temperature is started to be raised from 20° to 50° C. and raised

TABLE 4

| | Conditions for reductive activation of catalyst | | | | | | Reduction | Catalyst performance | |
|---|---|---|---|---|---|---|---|---|---|
| | Atmosphere | LHSV | Pressure (kg/cm$^2$) | H$_2$ concentration (%) | T$_1$ (°C.) | T$_2$ (°C.) | percent (%) | Relative activity | Selectivity |
| Example 12 | Liquid phase | 0.5 | 20 | 100 | 130 | 200 | 80 | 1.23 | 0.50 |
| Comparative Example 5 | Gas phase | — | 15 | 1.3–5.0 | 130 | 200 | 100 | 1 | 1 |

Relative activity, selectivity: Relative values based upon the catalyst performance of the catalyst activated by gas phase reduction in Comparative Example 5. Catalyst: Copper-iron-chromium catalyst Comparative Example 5

The formed catalyst precursor described in Example 12 was subjected to gas phase reduction under the same conditions as in Comparative Example 1. Using the catalyst thus activated by gas phase reduction, hydrogenation of a fatty acid methyl ester was carried out according to the method described in Example 1. The results are shown in Table 4.

These results demonstrate that all catalysts prepared by the method for preparing a copper-containing hydrogenation over at least 1.5 hours in the range of from 70° C. to 140° C. continuously or discontinuously in the first stage of liquid phase reduction.

3. The method according to claim 1, wherein the temperature is started to be raised from 20° C. to 50° C. in the first stage of liquid phase reduction.

4. The method according to claim 1, wherein the rate at which the temperature is raised is in the range of 0.5 to 40° C./hr.

5. The method according to claim 1, wherein the rate for supplying the hydrogen gas or the mixture of hydrogen and inert gas is in the range of from 50 to 10000/hr as a gas hourly space velocity.

6. The method according to claim 1, wherein the rate for supplying the solvent is in the range of from 0.1 to 5.0/hr as a liquid hourly space velocity.

7. The method according to claim 1, wherein 20 to 95% by weight of the copper oxide contained in the catalyst precursor is reduced in the first stage of liquid phase reduction.

8. The method according to claim 1, wherein the solvent which does not react with copper oxide or metallic copper is one or more members selected from the group consisting of glyceride oils, fatty acid esters, aliphatic alcohols and hydrocarbons.

9. The method according to claim 1, wherein the precursor of the copper-containing hydrogenation reaction catalyst is one member selected from the group consisting of precursors for copper-chromium oxide catalysts, copper-zinc oxide catalysts, copper-iron oxide catalysts, copper-aluminum oxide catalyst and copper-silica oxide catalysts.

10. The method according to claim 1, wherein the content of copper oxide is in the range of from 5 to 98% by weight per the total weight of the catalyst precursor.

11. The method according to claim 1, wherein reductive activation is carried out in a fixed bed reactor.

12. A method for producing an alcohol, comprising the step of reducing an organic carboxylic acid or ester of organic carboxylic acid by catalytic reduction with hydrogen in a fixed bed continuous reaction system, using the catalyst prepared by the method of any one of claims 1 to 11.

13. A method for producing an alcohol, comprising the steps of:

(a) reducing a formed precursor of a copper-containing hydrogenation reaction catalyst in a fixed bed continuous reactor with hydrogen gas or a mixture of hydrogen and inert gas by liquid phase reduction in a stream of a solvent which does not react with copper oxide or metallic copper, so as to obtain a catalyst, which comprises the steps of performing the first stage of liquid phase reduction by which the catalyst precursor is activated in the temperature range of from 20° to 140° C. so that at least 10% by weight of the copper oxide contained in the catalyst precursor can be reduced by the time when the temperature passes 140° C., and then performing the second stage of liquid phase reduction by which the catalyst precursor is further activated in the temperature range of from 140° to 250° C.; and (b) subsequently, reducing an organic carboxylic acid or ester of organic carboxylic acid by catalytic reduction with hydrogen in said fixed bed continuous reactor, using the catalyst activated in the step (a).

\* \* \* \* \*